(12) United States Patent
Yang et al.

(10) Patent No.: US 12,078,034 B2
(45) Date of Patent: Sep. 3, 2024

(54) CRACKING PERMEABILITY INCREASING METHOD COMBINING HYDRAULIC FRACTURING AND METHANE IN-SITU COMBUSTION EXPLOSION

(71) Applicant: CHINA UNIVERSITY OF MINING AND TECHNOLOGY, Suzhou (CN)

(72) Inventors: Wei Yang, Suzhou (CN); Zening Wei, Suzhou (CN); Cheng Zhai, Suzhou (CN); Yihan Wang, Suzhou (CN); Wenyuan Wang, Suzhou (CN); Wenxiao Zhang, Suzhou (CN)

(73) Assignee: CHINA UNIVERSITY OF MINING AND TECHNOLOGY (CN)

( * ) Notice: Subject to any disclaimer, the term of this patent is extended or adjusted under 35 U.S.C. 154(b) by 0 days.

(21) Appl. No.: 18/027,605

(22) PCT Filed: Dec. 27, 2021

(86) PCT No.: PCT/CN2021/141463
§ 371 (c)(1),
(2) Date: Mar. 21, 2023

(87) PCT Pub. No.: WO2022/252591
PCT Pub. Date: Dec. 8, 2022

(65) Prior Publication Data
US 2024/0110465 A1    Apr. 4, 2024

(30) Foreign Application Priority Data

May 31, 2021  (CN) .......................... 202110598931.6

(51) Int. Cl.
*E21B 34/06*  (2006.01)
*E21B 43/00*  (2006.01)
(Continued)

(52) U.S. Cl.
CPC .......... *E21B 43/006* (2013.01); *E21B 34/066* (2013.01); *E21B 43/1185* (2013.01);
(Continued)

(58) Field of Classification Search
CPC ...... E21B 43/16; E21B 43/006; E21B 34/066; E21B 43/248; E21B 43/263; E21B 49/00; E21B 7/046; B01N 33/0027
See application file for complete search history.

(56) References Cited

U.S. PATENT DOCUMENTS

| | | | |
|---|---|---|---|
| 4,045,085 A | 8/1977 | Garrett | .............................. 299/2 |
| 4,151,877 A * | 5/1979 | French | .................. E21B 43/247 |
| | | | 166/250.15 |

(Continued)

FOREIGN PATENT DOCUMENTS

| | | | | |
|---|---|---|---|---|
| CN | 101558216 | 10/2009 | ............. | E21B 43/17 |
| CN | 101563524 | 10/2009 | ............. | E21B 43/24 |

(Continued)

*Primary Examiner* — Silvana C Runyan
(74) *Attorney, Agent, or Firm* — HAYES SOLOWAY P.C.

(57) ABSTRACT

A method for shale gas exploitation includes performing horizontal drilling operation on an area to be constructed, forming a crack around a horizontal drill hole wall by shaped charge perforation; expanding the crack around a horizontal hole hydraulic fracturing, and extracting methane gas after a fracturing fluid is discharged; after methane gas is reduced, performing in-situ combustion explosion fracturing on the methane involved in horizontal drilling; thereafter continuing to expand the crack in the horizontal drill hole such that methane continues to seep out, and continuing extracting methane; repeating combustion explosion fracturing and extraction operations, so as to increase combustion explosion cracking permeability, and greatly enhance the exploitation effect of shale gas. The method is suitable for fracturing reconstruction of unconventional oil and gas (Continued)

reservoirs such as shale gas reservoirs, coal seam gas reservoirs and tight sandstone gas reservoirs.

9 Claims, 5 Drawing Sheets

(51) Int. Cl.
*E21B 43/1185* (2006.01)
*E21B 43/248* (2006.01)
*E21B 43/263* (2006.01)
*E21B 49/00* (2006.01)
*G01N 33/00* (2006.01)
*E21B 7/04* (2006.01)

(52) U.S. Cl.
CPC .......... *E21B 43/248* (2013.01); *E21B 43/263* (2013.01); *E21B 49/00* (2013.01); *G01N 33/0027* (2013.01); *E21B 7/046* (2013.01)

(56) References Cited

U.S. PATENT DOCUMENTS

| | | | |
|---|---|---|---|
| 2008/0087427 A1 | 4/2008 | Kamisnsky et al. | 166/272.1 |
| 2008/0087428 A1 | 4/2008 | Symington et al. | 166/272.2 |
| 2009/0308613 A1* | 12/2009 | Smith | E21B 43/2607 |
| | | | 166/305.1 |
| 2010/0012331 A1* | 1/2010 | Larter | E21B 43/243 |
| | | | 166/401 |
| 2015/0345268 A1* | 12/2015 | Bryant | C09K 8/62 |
| | | | 507/202 |
| 2019/0112909 A1 | 4/2019 | Zeng et al. | E21B 43/26 |
| 2021/0148205 A1 | 5/2021 | Lin et al. | E21B 43/247 |

FOREIGN PATENT DOCUMENTS

| | | | |
|---|---|---|---|
| CN | 105626028 | 6/2016 | E21B 43/27 |
| CN | 109025937 | 12/2018 | E21B 43/26 |
| CN | 110454131 | 11/2019 | E21B 43/263 |
| CN | 112761588 | 5/2021 | E21B 43/00 |
| CN | 113294134 | 8/2021 | E21B 43/26 |
| WO | WO-2014044192 A1 * | 3/2014 | E21B 41/0064 |

* cited by examiner

CRACKING PERMEABILITY INCREASING METHOD COMBINING HYDRAULIC FRACTURING AND METHANE IN-SITU COMBUSTION EXPLOSION

TECHNICAL FIELD

The present invention relates to a method for increasing permeability by cracking, and particularly relates to a method for increasing permeability by a synergetic cracking formed by hydraulic fracturing and in-situ combustion and explosion of methane, which is suitable for use in exploitation of the shale gas reservoir.

BACKGROUND ART

Shale gas refers to an unconventional natural gas, which lies in shale with rich organic matter and its interlayer in an adsorption state, a free state or a dissolved state. Shale gas together with gas reservoirs in coal seam and gas reservoirs in compact sandstone are called three unconventional gas reservoirs. The main components of shale gas is methane, mixed with ethane and propane, and the shale gas has the characteristics such as long mining period, cleanness, high efficiency. The shale gas has become one of the best alternative energy sources to coal in the industrial development process. Shale gas resources in China are abundant, the available resource amount of which reaches 36.1 trillion $m^3$. Efficient development of shale gas resources will make up for the demand gap of natural gas of China in the future, and will deeply affect the energy structure of China, which is of great significance to ensuring the energy security of China. The shale reservoir has an obvious feature of a low porosity (<5%) and a low permeability (<0.001×$10^{-3}$ $\mu m^2$), which causes difficulty to the development and utilization of shale gas. Therefore, the shale reservoir must be subjected to artificial fracturing transformation to form a communicated fracture network, thereby achieving the purpose of increasing the gas production amount produced from the shale.

Performing fracturing transformation on a shale reservoir by using a hydraulic fracturing technology to obtain an industrial gas flow is a main manner for exploiting shale gas at present. The staged fracturing technology with horizontal well is a mainstream technology for currently developing unconventional reservoirs such as shale gas and tight oil, and refers to the transformation of reservoir by lowering the drill rod to a target layer with a steering technology on the basis of a vertical shaft and injecting a plenty of fracturing liquid so as to fracture the target layer. Under the action of the continuously injected high-pressure fracturing fluid, the pressure in the natural fracture exceeds the closing pressure, the natural fracture is opened, and the rock generates shear slip, achieving the communication between the natural fracture and the rock bedding. With this technology, the transformation volume of the reservoir can be increased, and the production capacity of the horizontal well is improved. In the United States, the shale reservoir is effectively reconstructed by utilizing technologies such as staged fracturing of horizontal well, synchronous fracturing, and shale gas development is rapidly developed; however, the shale gas reservoir in China has obvious difference with the United States in the aspects such as geological characteristics, burial depth of reservoir, and technical conditions of fracturing. The successful experience of shale gas exploitation in the United States cannot be directly applied to China.

The burial depth of shale gas in Sichuan, Chongqing and the like in China is generally 2,600 m to 3,000 m, the burial depth of the shale gas reservoir in deep stratum is 4,000 m or above, the shale reservoir is compact, the pressure coefficient is high, and the fracturing difficulty is high. High-energy gas fracturing mainly utilizes high-pressure gas generated by explosion of gunpowder such as a rapid curing liquid explosive or a rocket propellant such as unsymmetrical dimethylhydrazine to fracture the rock mass, so that the reservoir generates micro-fractures, which has the characteristics of low cost and low pollution, but also has the problems such as poor safety of initiating explosive products, small propagation scale of fractures.

SUMMARY OF THE INVENTION

In view of the drawbacks in the prior art, the present invention provides a method for increasing permeability by a synergetic cracking formed by hydraulic fracturing and in-situ combustion and explosion of methane, which could make full use of the respective advantage of hydraulic fracturing and fracturing by energy-gathered combustion and explosion, the permeability of the shale reservoir is increased by a synergetic cracking, wherein, an energy-gathered perforating technology is utilized to form pore passages in a compact shale reservoir, which works with hydraulic fracturing to extend and develop the pore passages into a main fracture and achieve the placement of a combustion improver into fractures, the methane gas desorbed in situ from the shale reservoir is taken as an explosion source and a pulsed and multi-phased fracturing by combustion and explosion is used.

In order to achieve the above objects, the method for increasing permeability by a synergetic cracking formed by hydraulic fracturing and in-situ combustion and explosion of methane, firstly, performing horizontal drilling construction on an area to be constructed, and then making fractures around the wall of the horizontal borehole by means of energy-gathered perforating; continuing to expand the fractures around the horizontal borehole by means of hydraulic fracturing method, and then performing methane extraction after the fracturing fluid is discharged; performing fracturing by in-situ combustion and explosion of methane involved in the horizontal borehole after the methane gas is reduced; after combustion and explosion, continuing to expand the fractures in the horizontal borehole so that the methane continues to seep out, and then continuing to perform extraction; repeating the fracturing by combustion and explosion and extraction operation, thereby achieving the permeability increasing by a synergetic cracking, and greatly enhancing the mining effect of the shale gas.

The specific steps are as follows:

S1: drilling vertical shaft towards the pre-fractured intervals in shale reservoir from the ground, after the fractured intervals and fractured positions in shale reservoir are determined; drilling a horizontal gas well with a steering to reach the pre-fractured position; arranging a casing in the horizontal gas well to form a casing string, and then arranging a pumping pipeline for fracturing fluid and a methane extraction pipeline in the vertical shaft connected to the horizontal gas well, wherein a methane gas concentration and flow detector is provided in the methane extraction pipeline;

S2: lowering the perforating gun loaded with the perforating bullet to the pre-fractured position in the shale reservoir through the casing string to make fractures by means of energy-gathered perforating, so as to generate a large number of conical thorn-shaped pore passages in the compact shale reservoir;

S3: taking out the perforating gun, injecting the fracturing fluid mixed with the combustion improver into the casing through the pumping pipeline for fracturing fluid by using the fracturing fluid storage tank, performing hydraulic fracturing on the shale reservoir by the fracturing fluid from perforated holes of the casing, performing fracturing on the reservoir by the fracturing fluid along the conical thorn-shaped perforation passage so that the conical thorn-shaped perforation passage is further opened and expanded into the main fracture; performing tension damage by the fracturing fluid, at the tip of the conical thorn-shaped perforation passage formed by the perforation hole, thereby constructing the main channel for the flow of methane and other fluids to the casing, fracturing and forming secondary fractures by hydraulic fracturing, around the main fracture; when the pumping pressure of the fracturing fluid is reduced to 30% of the peak pressure, the pumping is stopped; the fracturing fluid is returned and discharged after the hydraulic fracturing process is finished, the combustion improver is retained in the fracture where the combustion improver enters to play a function of auxiliary support;

S4: after the return and discharge of the fracturing fluid is finished, the desorption amount of methane gas in the shale reservoir is increased; at this time, the solenoid valve I is closed and the solenoid valve II is opened, the methane extraction pump is started to perform methane extraction through the methane extraction pipeline; the methane gas concentration and the gas flow rate in the extraction pipeline are monitored in real time with the methane gas concentration and flow detector arranged on the rock gas extraction pipeline; when the methane gas concentration and flow detector detects that the extracted methane gas flow rate is stable and kept above a preset value, it is determined that it is a stable extraction stage and the methane gas concentration currently monitored is considered to be the same as the gas concentration desorbed in real time; at this time, the casing string is used as a gas extraction pipeline at the horizontal gas well section;

S5: when the methane gas concentration and flow detector monitors that the methane concentration changes in real time during the extraction process, the extraction operation is stopped after the concentration of the methane gas in the entire space of the pipeline and the fractures during the extraction process is reduced to the detonation concentration, according to the natural attenuation characteristic of the gas concentration in the extraction borehole; lowering the detonation device to the wellhead of the horizontal gas well, and igniting the methane desorbed in situ from the reservoir fractures by the detonation device to induce combustion and explosion; the detonation device includes an electric spark igniter, a transmission cable and a ground intelligent controller, the process of combustion and explosion induced by igniting is as follows: the ground intelligent controller closes the solenoid valve I and the solenoid valve II, current flows into the electric spark igniter through the transmission cable to generate electric sparks so as to induce the methane deflagration;

S6: after the deflagration, a new fracture network which is more complex is formed in the horizontal gas well to facilitate desorption and migration of methane gas, so that the methane gas concentration in the horizontal gas well is increased again; at this time, the solenoid valve II is opened again to continue gas extraction; after the methane gas concentration is reduced again, the step S5 is repeated to perform fracturing by combustion and explosion of methane again; the above steps are repeated to realize the permeability increasing of shale reservoir by a synergetic cracking formed by hydraulic fracturing and in-situ combustion and explosion of methane in multiple stages, thus a three-dimensional fracture network is constructed step by step, more methane occurring in the reservoir is desorbed, collected into the casing string, and conveyed to a place above the well through the methane extraction pipeline; the fracturing and extraction operation of this interval will be finished if the increase rate of the methane extraction amount is lower than 10%.

Furthermore, a cement sheath formed by pouring cement is arranged between the outer side of the casing string and the well wall to fix the casing string, the casing string is connected with the vertical shaft through a steering, a metal sealing sleeve is installed at the connection of the casing string and the pipeline in the vertical shaft, the solenoid valve I is installed on the pumping pipeline for fracturing fluid, the solenoid valve II is installed on the methane extraction pipeline, the solenoid valve I and the solenoid valve II are connected with an intelligent controller arranged on the ground through connecting lines.

Furthermore, making fractures by energy-gathered perforating refers to: lowering the perforating gun loaded with the perforating bullet to the pre-fractured position in the shale reservoir through the casing string, the perforating gun is electrically detonated, the perforating bullet in the perforating bullet trough is ejected from the perforating hole, and the generated high-temperature and high-pressure shock waves penetrate through the casing string to form conical thorn-shaped pore passages in the shale reservoir, so that fracture-making of the compact shale reservoir at early stage is achieved;

Furthermore, after the perforating gun is taken out, the solenoid valve I is opened and the solenoid valve II is closed by the ground intelligent controller to perform hydraulic fracturing operation on the shale reservoir: fracturing fluid enters the casing along the pumping pipeline for fracturing fluid from the fracturing fluid storage tank to fracture the shale reservoir, the conical thorn-shaped pore passages are further opened and expanded into the main fracture, and then the secondary fractures formed by hydraulic fracturing are formed around the main fracture.

Furthermore, the combustion improver is in the form of solid particle, which includes potassium permanganate spheres, aluminum powder and magnesium powder; the combustion improver is doped into the fracturing fluid, so that the combustion improver is injected into the formed fractures along with the hydraulic fracturing process; in order to ensure that the particles of combustion improver enter into the fracturing fractures, the displacement fluid is pumped, after the fracturing fluid returns and discharges, the combustion improver is retained in the formed fractures for supporting.

Furthermore, the detonation concentration refers to that the concentration measured by the methane gas concentration and flow detector is within the range of 8% to 11%.

Furthermore, when there is a need to perform fracturing by combustion and explosion of methane again in step S6, the hydraulic fracturing process can be performed again, and the combustion improver can be added synchronously.

BENEFICIAL EFFECTS

1. The advantages of long extension range of hydraulic fracturing fractures and complex fractures induced by in-situ combustion and explosion of methane in multiple stages are fully exerted, the two technologies are combined to achieve permeability increasing of the shale reservoir by synergetic cracking, effectively increasing the fracture density, and better expanding transformation volume of the reservoir (SRV);
2. The delivery mode of the combustion improver is novel, that is, the combustion improver is doped into the fracturing fluid and delivered during the hydraulic fracturing process, so that fracture fracturing and combustion improver delivery are synchronously carried out;
3. Based on the process characteristics of traditional hydraulic fracturing in which the sand is carried into fractures, a combustion improver in form of solid particle is used to replace a propping agent, so as to avoid a re-occlusion of the smooth fractures formed by hydraulic fracturing under the influence of stress and the like, guarantee the flow conductivity of the reservoir, assist methane combustion and explosion in the subsequent process, and realize the fracturing of reservoir by in-situ combustion and explosion of methane at the fractures;
4. The use of energy-gathered perforating for making fracture at early stage significantly reduces the crack initiation pressure for the subsequent hydraulic fracturing and reduces the construction difficulty. The in-situ combustion and explosion of methane is used to impact and fracture the shale reservoir, which is conducive to the generation of laterally derived fractures and the construction of three-dimensional fracture network. At the same time, the weakness that traditional hydraulic fracturing is difficult to effectively achieve the yield increase of the gas reservoir in the deep compact shale is remedied, and the transformation effect is improved.

In the figures: 1—ground, 2—overlying stratum, 3—shale roof, 4—shale reservoir, 5—shale floor, 6—fracturing fluid storage tank, 7—methane extraction pump, 8—pumping pipeline for fracturing fluid, 9—methane extraction pipeline, 10—vertical shaft, 11—steering, 12—horizontal gas well, 13—casing string, 14—cement sheath, 15—metal sealing sleeve, 16—solenoid valve I, 17—solenoid valve II, 18—casing, 19—perforation holes, 20—perforating bullet trough, 21—conical thorn-shaped pore passage, 22—main fracture, 23—secondary fractures by hydraulic fracturing, 24—ground intelligent controller, 25—connecting line, 26—methane gas concentration and flow detector, 27—electric spark igniter, 28—transmission cable, 29—three-dimensional fracture network, 30—perforating gun.

EMBODIMENTS

Figure 1:
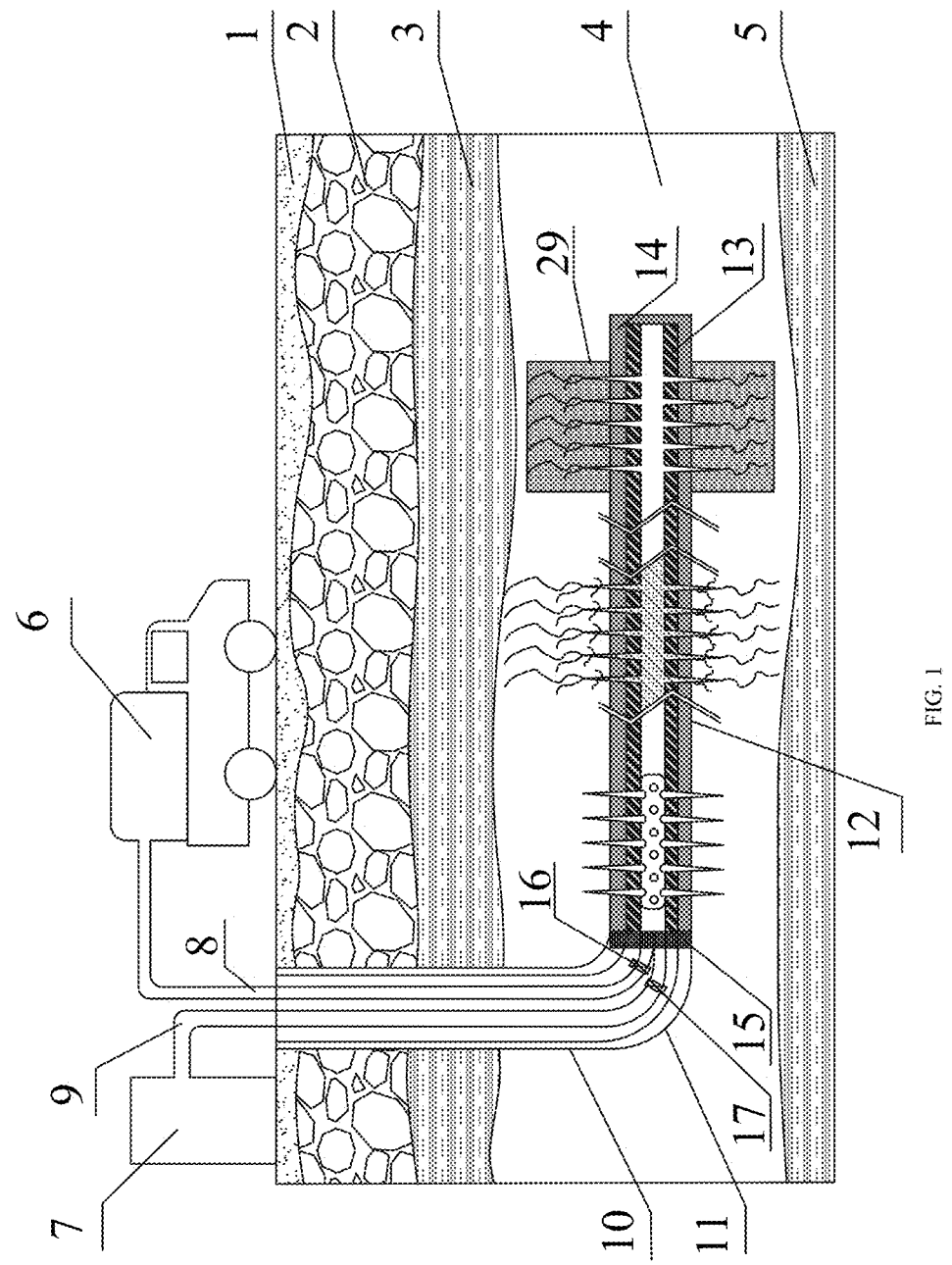
FIG. 1 is a schematic diagram of permeability increasing of shale reservoir by a synergetic cracking formed by hydraulic fracturing and in-situ combustion and explosion of methane according to an example of the present invention.

The embodiments of the present invention will be further described below with reference to the accompanying drawings:

As shown in FIG. 1, the method for increasing permeability by a synergetic cracking formed by hydraulic fracturing and in-situ combustion and explosion of methane, comprising the following steps:
(1) Preparation Work for Drilling.

The positions of the shale roof 3 and the shale floor 5 are explored and determined through early geological exploration, the fracturing interval and the fracturing position in the shale reservoir 4 are determined; starting to drill the vertical shaft 10 toward the pre-fractured interval in the shale reservoir 4 from the ground 1; the shaft passes through the overlying stratum 2, the shale roof 3 and then into the shale reservoir 4; the horizontal gas well 12 is drilled with the steering 11 to reach the pre-fractured position. Then, the casing is lowered to the section of horizontal well, and the casings are sealed and connected with each other to form the casing string 13 for supporting the shale gas well, in particular for supporting the hole wall after methane deflagration, and at the same time, it plays a role in constructing the transportation and extraction pipelines for fracturing fluid and methane gas. The cement sheath 14 formed by pouring cement is arranged between the casing string 13 and the well wall to fix the casing string 13; the casing string 13 communicates with the vertical shaft 10, specifically, the pumping pipeline 8 for fracturing fluid and the methane extraction pipeline 9 are arranged in the vertical shaft 10. A metal sealing sleeve 15 is installed at the connection of the casing string 13 and the pipeline in the vertical shaft 10. The solenoid valve I 16 is installed on the pumping pipeline 8 for fracturing fluid, and the solenoid valve II 17 is installed on the methane extraction pipeline 9. The solenoid valves are connected to the ground intelligent controller 24 through the connecting line 25.
(2) Making Fractures by Energy-Gathered Perforating.

Figure 2:
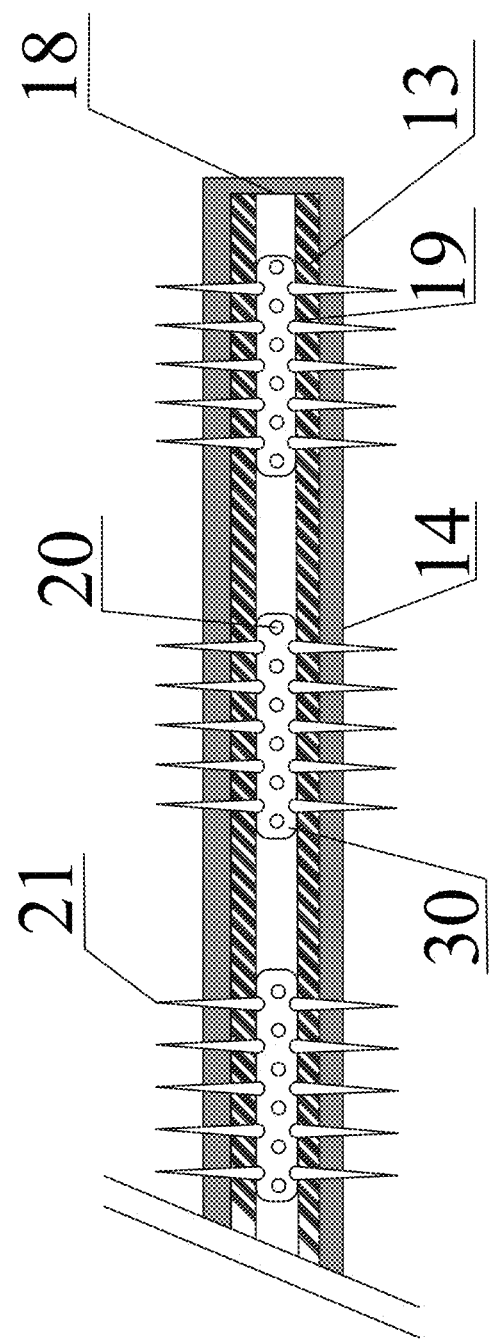
FIG. 2 is a schematic diagram of making fractures by energy-gathered perforating according to an example of the present invention.

Perforating holes 19 are formed in the body of the casing 18, the perforating holes 19 are arranged in a staggered mode in the circumferential direction and the axial direction of the casing 18. The perforating bullet trough 20 in the perforating gun 19 is aligned to form a directional energy-gathered jet. Making fractures by energy-gathered perforating refers to that the perforating gun 19 carrying the perforating bullet is lowered to the pre-fractured position of the shale reservoir 4 through the casing string 13, the perforating gun 19 uses an electrically detonated mode, after the detonating switch is turned on, the pin transmits the current to the detonator, the detonator detonates to eject out the perforating bullet in the perforating bullet trough 20, and the generated high temperature and high-pressure shock waves penetrate the casing string 13 to form the conical thorn-shaped pore passages 21 in the shale reservoir 4, so as to realize the fracture making of the compact shale reservoir 4 at early stage. After detonation, a large amount of energy will be gathered in the casing 18, and intensively released from the unrestrained perforating holes 19. This high-energy and high-speed shock wave generates a huge impact on the surrounding shale, and forms conical thorn-shaped pore passages 21 in the length of dozens of centimeters. The perforating bullet trough 20 is staggered along the gun body of perforating gun 19, forming a three-dimensional pore passage system in space, as shown in FIG. 2.

(3) Hydraulic Fracturing Operation.

Figure 3:
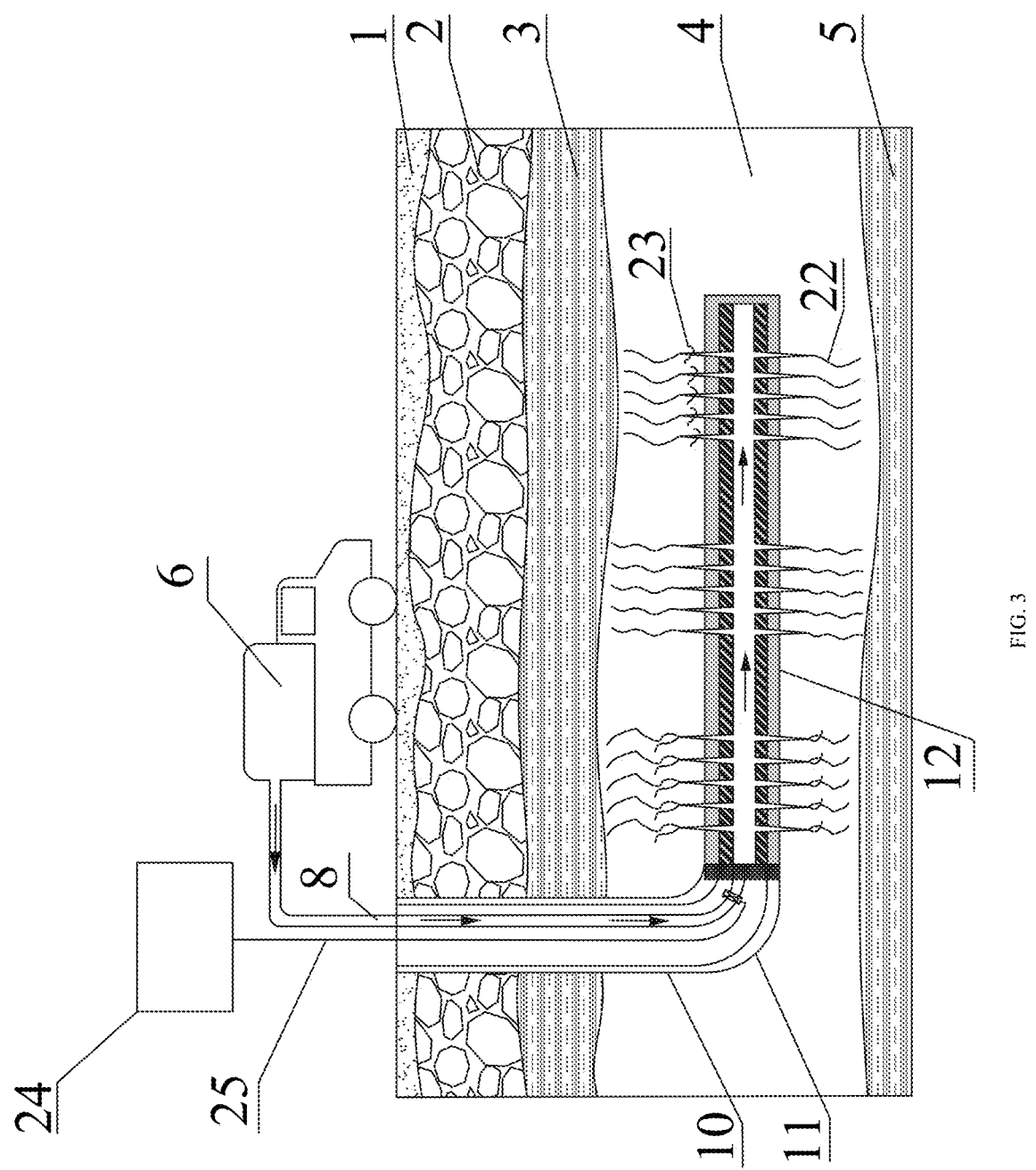
FIG. 3 is a schematic diagram of a hydraulic fracturing process and the fracture development in a shale reservoir according to an example of the present invention.

After the fracturing making by the energy-gathered perforating is completed, the perforating gun 19 is taken out, the ground intelligent controller 24 opens the solenoid valve I 16 and closes the solenoid valve II 17 to perform hydraulic fracturing operation on the shale reservoir 4; the fracturing fluid fractures the reservoir along the pore passages so as to further open and expand the original pore passage to form a main fracture 22; the fracturing fluid conducts tension damage at the tip of the pore passage formed by the energy-gathered perforating to form a hydraulic fracture of hundred meter level, constructing the main channel for the flow of fluids such as methane to the casing, and forming secondary fractures 23 by hydraulic fracturing around the main fracture. The combustion improver is in the form of solid particle, which is doped into the fracturing fluid, so that the combustion improver is injected into the formed fractures along with the hydraulic fracturing process. When the hydraulic fracturing fracture extends to a predetermined length and the injected combustion improver particles reach a predetermined number, the hydraulic fracturing operation is stopped, and the combustion improver is retained in the formed fractures for supporting, as shown in FIG. 3.

In order to better realize fracturing of fractures and the delivery of combustion improver into the fractures, a mode of injecting low-viscosity fracturing liquid and high-viscosity fracturing liquid according to different phases is used in the hydraulic fracturing process, that is, the fracturing fluid with the viscosity of 40±10 mPa·s is utilized to carry 100-mesh combustion improver particles at the initial stage of fracturing, so that the low-viscosity fracturing fluid can reduce the frictional resistance of the fracture surface, and the fine particles have a certain blocking effect on natural fractures near the casing so as to facilitate the outward extension of the main fracture; meanwhile, the fine particles are easier to enter secondary tiny fractures formed in the fracturing process; at the later stage of fracturing, the fracturing fluid with a viscosity of 80±10 mPa·s is utilized to carry a 30-mesh combustion improver particle so that the main fracture is supported and the width of the main fracture is increased to ensure that the main fracture extends to the deep region; the higher the viscosity of the fracturing fluid is, the stronger the sand carrying capability is; the combustion improver of a larger particle size can be carried, improving the flow conductivity of the main fracture and ensuring the combustion and explosion effect of methane; more preferably, a displacement fluid can be injected so as to enable the combustion improver to better enter the fractures. More preferably, the combustion improver particles may use potassium permanganate, potassium perchlorate, magnesium powder, aluminum powder, etc.

(4) Methane Extraction.

Figure 4:
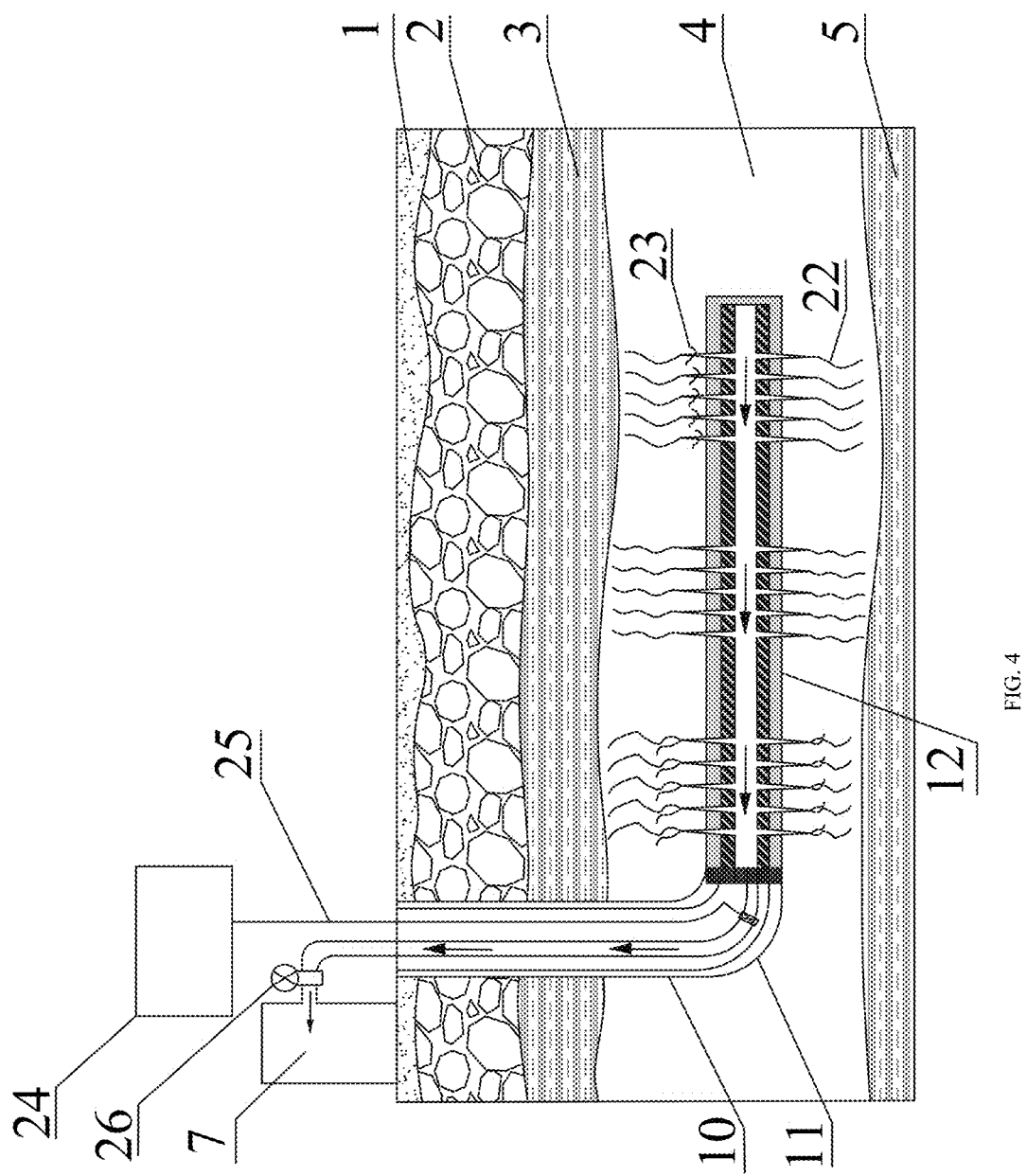
FIG. 4 is a schematic diagram of methane extraction after hydraulic fracturing of the shale reservoir according to an example of the present invention.

After the hydraulic fracturing operation, the desorption amount of methane gas from the shale reservoir 4 is increased; the methane gas concentration and flow detector 26 is arranged on the methane extraction pipeline 9, which is configured to monitor the methane gas concentration desorbed from the fracturing area in real time. When the gas concentration reaches the extraction standard, the ground intelligent controller 24 opens the solenoid valve II 17 and closes the solenoid valve I 16 for methane extraction. The casing string 13 is used as a gas extraction pipeline for collecting and delivering the shale gas, as shown in FIG. 4.

(5) Fracturing by In-Situ Combustion and Explosion of Methane.

Figure 5:
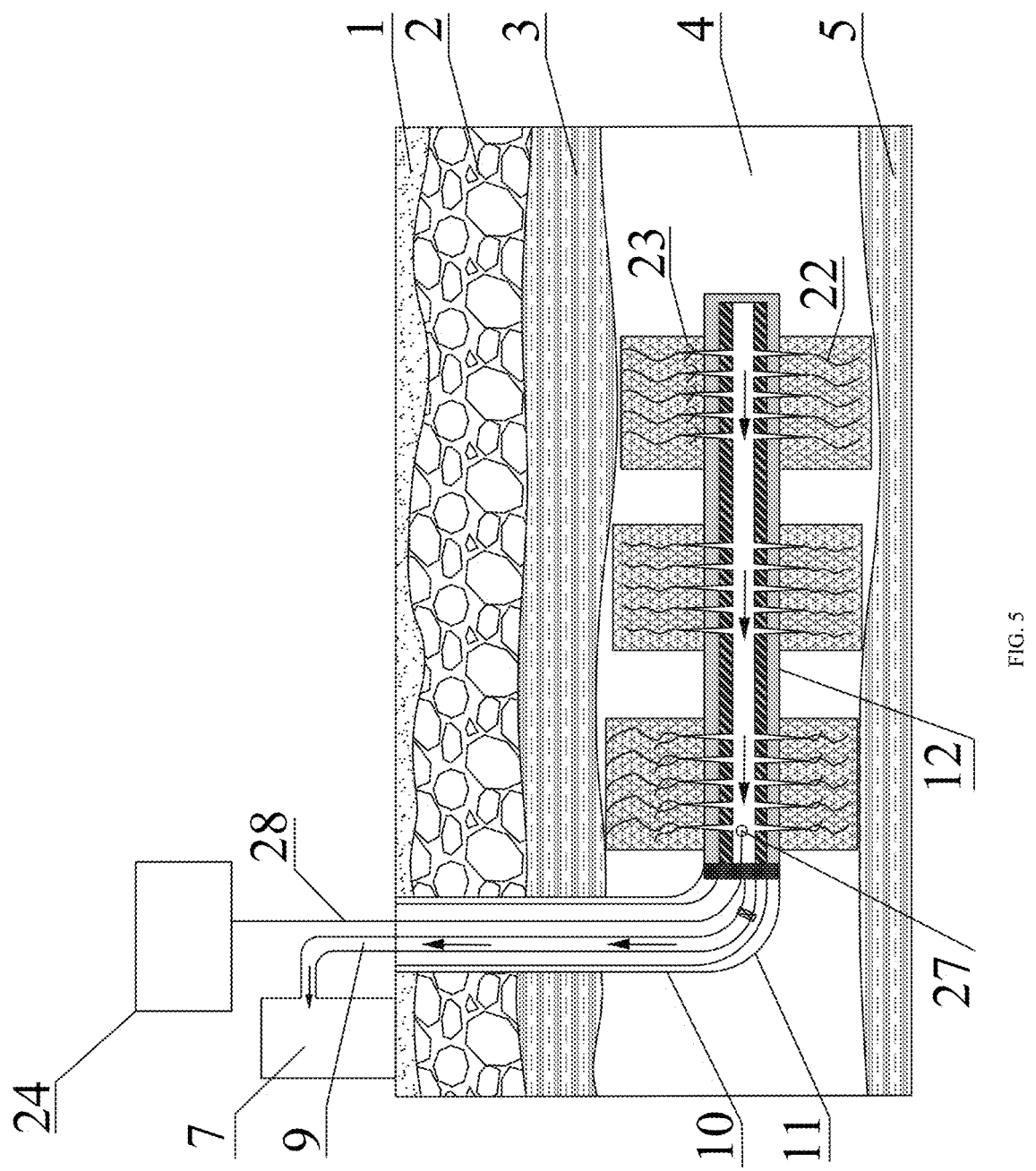
FIG. 5 is a schematic diagram of methane extraction and fracture network after in-situ combustion and explosion in the shale reservoir according to an example of the present invention.

The concentration of methane in the reservoir fractures is monitored in real time by the methane gas concentration and flow detector 26, the methane in-situ desorbed from the reservoir fractures is ignited by the detonation device to induce deflagration after the concentration of the methane gas in the entire space of the pipeline and the fractures reaches the detonation concentration during the extraction process, according to the natural attenuation characteristic of the gas concentration of the extraction borehole. The detonation device includes an electric spark igniter 27, a transmission cable 28 and a ground intelligent controller 24, wherein the detonation concentration refers to that the concentration measured by the methane gas concentration and flow detector is within the range of 8% to 11%, the detonation process induced by ignition is that the ground intelligent controller 24 closes the solenoid valve I 16 and the solenoid valve II 17, current flows into the electric spark igniter 27 through the transmission cable 28 to generate electric sparks for inducing methane deflagration; more preferably, the optimal deflagration point of methane is about 9.5%, at this time, the chemical reaction reacts completely and the generates the largest temperature and pressure, as shown in FIG. 5.

(6) Continuing Extraction after Combustion and Explosion.

After the shale reservoir 4 is subjected to combustion and explosion to increase permeability, a more complex fracture is formed, the extraction concentration and flow rate of methane are increased, and the extraction operation is continued to be performed according to step (4).

(7) Pulsed Fracturing by Energy-Gathered Combustion and Explosion in Multiple Stages.

After the methane concentration is reduced again, performing the fracturing by combustion and explosion of methane; when necessary, a hydraulic fracturing process can be performed, and a combustion improver can be added synchronously. In this way, the above steps are repeated to realize permeability increasing of the shale reservoir by a synergetic cracking formed by hydraulic fracturing and in-situ combustion and explosion of methane in multiple stages, thus the three-dimensional fracture network 29 is constructed step by step, more methane occurring in the reservoir is desorbed and collected into the casing string 13 and conveyed to a place above the well through the methane extraction pipeline 8 until the fracturing and extraction operation of all the intervals is completed.

In view of the problem of fracturing transformation of unconventional oil and gas reservoirs such as shale reservoir, the present invention provides a method for increasing permeability by a synergetic cracking formed by hydraulic fracturing and in-situ combustion and explosion of methane. On the basis of a relatively mature energy-gathered perforating technology and a hydraulic fracturing technology, methane desorbed in-situ is used for combustion and explosion to carry out secondary transformation to the reservoir, and the drainage area of the reservoir and the range of fracture network are comprehensively improved. The effect of in-situ combustion and explosion of methane on the shale reservoir mainly comprises: firstly, a mechanical effect of high-temperature and high-pressure explosion, which is used for crushing a compact reservoir and generating a large number of micro-fractures; secondly, a stress wave effect to deform and destroy the rock; thirdly, a replacement effect, wherein, the adsorption capacity of $CO_2$ molecules in the product of combustion and explosion of methane is greater than that of methane molecules, the $CO_2$ with stronger adsorption capacity can replace the adsorbed methane in the reservoir; fourthly, a chemical effect, an acidic gas such as $CO_2$ and $SO_2$ generated by explosion is dissolved in water to form an acidic solution that acidly corrodes the shale reservoir; and fifthly, a thermal effect, wherein the underground high-temperature environment generated by deflagration can significantly reduce the methane adsorption potential and facilitate the desorption and flow of methane. In summary, transformation of the shale reservoir and methane extraction efficiency can be effectively improved by utilizing a method for increasing permeability by a synergetic cracking formed by hydraulic fracturing and in-situ combustion and explosion of methane.

The invention claimed is:

1. A method for increasing permeability by a synergetic cracking formed by hydraulic fracturing and in-situ combustion and explosion of methane, comprising:

performing horizontal drilling construction on an area to be constructed, and then making fractures around a wall of a horizontal borehole by using an energy-gathered perforating; continuing to expand fractures around the horizontal borehole injecting fracturing fluids of different relative viscosities at different stages, and then performing methane extraction after a fracturing fluid is discharged; after the methane gas is reduced, performing fracturing by in-situ combustion and explosion of methane involved in the horizontal borehole; that is, after a concentration of methane in an entire space of a pipeline and the fractures during an extraction process is reduced to a detonation concentration, an extraction operation is stopped, methane desorbed in situ from reservoir fractures is ignited by a detonation device which includes an electric spark igniter to induce a combustion and explosion after the combustion and explosion, continuing to expand the fractures in the horizontal borehole so that the methane continues to seep out, and then continuing to perform extraction; repeating a fracturing by the combustion and explosion and the extraction operation, thereby achieving the permeability increasing by a synergetic cracking formed by the combustion and explosion, and enhancing a mining effect of a shale gas, and wherein the specific steps are as follows:

(1) after determining a fractured interval and a fractured position in a shale reservoir, drilling a vertical shaft toward a pre-fractured interval in the shale reservoir from a ground, drilling a horizontal gas well with a steering to reach a pre-fractured position, arranging a casing in a horizontal gas well to form a casing string, and then arranging a pumping pipeline for fracturing fluid and a methane extraction pipeline in the vertical shaft connected to a horizontal gas well, wherein a methane gas concentration and flow detector is provided on the methane extraction pipeline;

(2) a perforating gun loaded with a perforating bullet is lowered to the pre-fractured position in the shale reservoir through the casing string to make fractures by energy-gathered perforating, so as to form a large number of conical thorn-shaped pore passages in a compact shale reservoir;

(3) taking out the perforating gun, injecting the fracturing fluid mixed with a combustion improver into the casing by utilizing a fracturing fluid storage tank through the pumping pipeline for fracturing fluid, the fracturing fluid performing hydraulic fracturing on the shale reservoir through perforation holes of the casing, fracturing a reservoir by the fracturing fluid along the conical thorn-shaped pore passage so that a conical thorn-shaped pore passage is further opened and expanded into the main fracture, performing tensile damage by the fracturing fluid, at a tip of the conical thorn-shaped pore passage formed by a perforation hole, thereby constructing a main channel for the flow of methane and other fluids to the casing; fracturing around the main fracture to form secondary fractures by hydraulic fracturing, when the pumping pressure of the fracturing fluid is reduced to 30% of a peak pressure, a pumping operation is stopped, and the fracturing fluid is returned and discharged after a hydraulic fracturing process is finished, a combustion improver retains in the fractures where a combustion improver enters into to play a function for auxiliary support;

(4) after the return and discharge of the fracturing fluid is finished, a desorption amount of methane gas from the shale reservoir is increased, at this time, a first solenoid valve I is closed and a second solenoid valve II is opened, a methane extraction pump is started to perform methane extraction through the methane extraction pipeline, a methane gas concentration and the gas flow rate in the extraction pipeline are monitored in real time by using a methane gas concentration and flow detector arranged on the methane extraction pipeline; when the methane gas concentration and flow detector detects that the extracted methane gas flow rate is stable and kept above a preset value, it is determined that at this time, it is a stable extraction stage, and the methane gas concentration currently monitored is considered to be the same as the gas concentration desorbed in real time; at this moment, the casing string is used as a gas extraction pipeline at the horizontal gas well section;

(5) when the methane gas concentration and flow detector monitors that the methane concentration changes during an extraction process in real time, stopping the extraction operation, lowering the detonation device to a wellhead of the horizontal gas well, and igniting the methane in situ desorbed from the reservoir fractures the detonation device to induce combustion and explosion, after the concentration of the methane gas in the entire space of the pipeline and the fractures is reduced to the detonation concentration during the extraction process, according to a natural attenuation characteristic of the gas concentration in the extraction borehole, the detonation device with an electric spark igniter, a transmission cable and a ground intelligent controller, a process of igniting to induce combustion and explosion is that the ground intelligent controller closes the first solenoid valve I and the second solenoid valve II, the current flows into the electric spark igniter through the transmission cable to generate electric sparks and induce methane deflagration; and (6) after a deflagration, a new fracture network which is more complex is formed in a horizontal gas well to facilitate desorption and migration of methane gas, so that the methane gas concentration in the horizontal gas well is increased again, at this time, the second solenoid valve II is opened again to continue gas extraction; after the methane gas concentration is reduced again, the step (5) is repeated to perform fracturing by combustion and explosion of methane again, steps (1) through (5) are repeated as such to realize the permeability increasing of shale reservoir by the synergetic cracking formed by hydraulic fracturing and in-situ combustion and explosion of methane at multiple stages, thus a three-dimensional fracture network is constructed step by step, more methane occurring in the reservoir is desorbed and collected into the casing string, and the methane is conveyed to a place above a well through the methane extraction pipeline, a fracturing and extraction operation of an interval is completed if an increase rate of a methane extraction amount is lower than 10%.

2. The method for increasing permeability by a synergetic cracking formed by hydraulic fracturing and in-situ combustion and explosion of methane according to claim 1, wherein making fractures by energy-gathered perforating is realized as follows: lowering the perforating gun loaded with the perforating bullet to the pre-fractured position in the shale reservoir through the casing string, the perforating gun uses an electrically detonated mode, the perforating bullet in the perforating bullet trough is ejected from the perforating hole, and the generated high-temperature and high-pressure shock waves penetrate through the casing string to form conical thorn-shaped pore passage in the shale reservoir, so that the fracture of the compact shale reservoir is performed at an early stage.

3. The method for increasing permeability by a synergetic cracking formed by hydraulic fracturing and in-situ combustion and explosion of methane according to claim 1, wherein the first solenoid valve is installed on the pumping pipeline for fracturing fluid, the second solenoid valve is installed on the methane extraction pipeline, the first solenoid valve and the second solenoid valve are connected to the ground intelligent controller arranged on the ground through connecting lines.

4. The method for increasing permeability by a synergetic cracking formed by hydraulic fracturing and in-situ combustion and explosion of methane according to claim 1, wherein after the perforating gun is taken out, the ground intelligent controller is used to open the solenoid valve I and close the solenoid valve II to perform hydraulic fracturing operation on the shale reservoir: fracturing fluid enters into the casing along the pumping pipeline for fracturing fluid from the fracturing fluid storage tank to fracture the shale reservoir, so that the conical thorn-shaped pore passage is further opened and expanded into the main fracture, and the secondary fractures by hydraulic fracturing are formed around the main fracture.

5. The method for increasing permeability by a synergetic cracking formed by hydraulic fracturing and in-situ combustion and explosion of methane according to claim 1, wherein a cement sheath formed by pouring cement is arranged between the outer side of the casing string and the well wall to fix the casing string.

6. The method for increasing permeability by a synergetic cracking formed by hydraulic fracturing and in-situ combustion and explosion of methane according to claim 1, wherein the casing string is connected with the vertical shaft through a steering, a metal sealing sleeve is installed at the connection of the casing string and the pipeline in the vertical shaft.

7. The method for increasing permeability by a synergetic cracking formed by hydraulic fracturing and in-situ combustion and explosion of methane according to claim 1, wherein the combustion improver is in the form of solid particles, and includes potassium permanganate spheres, aluminum powder and magnesium powder, the combustion improver is doped into the fracturing fluid, so that the combustion improver is injected into the formed fractures during the hydraulic fracturing process; in order to ensure that the particles of combustion improver enter into the fracturing fractures, a displacement fluid is injected for assistance, after the fracturing fluid is returned and discharged, the combustion improver is retained in the formed fractures for supporting.

8. The method for increasing permeability by a synergetic cracking formed by hydraulic fracturing and in-situ combustion and explosion of methane according to claim 1, wherein the detonation concentration refers to that the concentration measured by the methane gas concentration and flow detector is within the range of 8% to 11%.

9. The method for increasing permeability by a synergetic cracking formed by hydraulic fracturing and in-situ combustion and explosion of methane according to claim 1, wherein in step (6), when there is a need to perform fracturing by combustion and explosion of methane again, the hydraulic fracturing process can be carried out again, and the combustion improver can be synchronously added.

* * * * *

UNITED STATES PATENT AND TRADEMARK OFFICE
CERTIFICATE OF CORRECTION

| | |
|---|---|
| PATENT NO. | : 12,078,034 B2 |
| APPLICATION NO. | : 18/027605 |
| DATED | : September 3, 2024 |
| INVENTOR(S) | : Yang et al. |

It is certified that error appears in the above-identified patent and that said Letters Patent is hereby corrected as shown below:

On the Title Page

Item (72) Inventors: Wei Yang, Suzhou (CN); Zening Wei, Suzhou (CN); Cheng Zhai, Suzhou (CN); Yihan Wang, Suzhou (CN); Wenyuan Wang, Suzhou (CN); Wenxiao Zhang, Suzhou (CN)"

Should be -- Item (72) Inventors: Wei Yang, Jiangsu (CN); Zening Wei, Jiangsu(CN); Cheng Zhai, Jiangsu (CN); Yihan Wang, Jiangsu(CN); Wenyuan Wang, Jiangsu (CN); Wenxiao Zhang, Jiangsu(CN) --.

Signed and Sealed this
Third Day of December, 2024

Katherine Kelly Vidal
*Director of the United States Patent and Trademark Office*